United States Patent
McBride (10) Patent No.: US 6,942,289 B2
(45) Date of Patent: Sep. 13, 2005

(54) WATER BASINS FOR HEAT STRAIN REDUCTION

(76) Inventor: Peter McBride, 184 Owl Drive, Ottawa, Ontario (CA), K1V 9P6

( * ) Notice: Subject to any disclaimer, the term of this patent is extended or adjusted under 35 U.S.C. 154(b) by 0 days.

(21) Appl. No.: 10/448,020

(22) Filed: May 28, 2003

(65) Prior Publication Data
US 2004/0201262 A1 Oct. 14, 2004

(30) Foreign Application Priority Data
Apr. 14, 2003 (CA) ................................. 2425530

(51) Int. Cl.[7] .............................. A47C 7/62; A47C 4/28
(52) U.S. Cl. ........................... 297/188.14; 297/180.15; 297/411.26; 297/411.43; 297/45
(58) Field of Search .................... 297/411.26, 411.43, 297/45, 188.14, 182, 180.15; 601/15, 17, 157, 158

(56) References Cited

U.S. PATENT DOCUMENTS

| | | | | |
|---|---|---|---|---|
| 2,091,167 A | * | 8/1937 | Solley | 607/86 |
| 3,001,208 A | * | 9/1961 | Rosoff | 4/622 |
| 3,245,716 A | * | 4/1966 | Danner | 297/163 |
| 3,625,434 A | * | 12/1971 | Kitover | 239/289 |
| 3,760,800 A | * | 9/1973 | Staffin et al. | 601/17 |
| 4,165,123 A | * | 8/1979 | Hutson | 297/153 |
| 5,000,384 A | * | 3/1991 | Arnold | 239/128 |
| 5,350,215 A | * | 9/1994 | DeMars | 297/188.14 |
| 5,441,477 A | * | 8/1995 | Hargest | 601/16 |
| 5,628,544 A | * | 5/1997 | Goodman et al. | 297/188.14 |
| 6,106,058 A | * | 8/2000 | Sur et al. | 297/188.19 |
| 6,149,238 A | * | 11/2000 | Tsai | 297/411.43 |
| 6,209,951 B1 | * | 4/2001 | Han | 297/45 |

* cited by examiner

Primary Examiner—Peter M. Cuomo
Assistant Examiner—Stephen D'Adamo
(74) Attorney, Agent, or Firm—Frommer Lawrence & Haug LLP; Ronald R. Santucci (57) ABSTRACT

A chair with water basins for heat strain reduction purpose is disclosed. The chair is provided with built-in or attachable water basins at the armrest level for the user to immerse his forearms and hands in the basins while seating on the chair. Another embodiment of the chair provides foot basin module detachably coupled to the chair with or without the hand basins, thereby enabling the user to immerse his feet in the water to enjoy the cooling effect. In the event where the user is standing up, the invention also teaches a hand and/or foot pool system so that an individual user or multiple users can immerse their extremities in water to cool off the body core temperature while standing up.

2 Claims, 7 Drawing Sheets

WATER BASINS FOR HEAT STRAIN REDUCTION

FIELD OF THE INVENTION

This application claims priority benefits of Canadian Patent Application Serial Number 2,425,530 filed Apr. 14, 2003.

This invention relates to a chair equipped with water basins and standing up water pools to enable the user to cool off his extremities in order to reduce heat strain.

BACKGROUND OF THE INVENTION

List of Prior Art Literatures

House, J. R., Holmes, C., and Allsopp, A. J. (1997) Prevention of Heat Strain by Immersing the Hands and Forearms in Water. *J Royal Naval Medical Service* 83.1:26–30.

House, J. R. (1998) Extremity Cooling as a Method for Reducing Heat Strain. *Journal of Defence Science Vol.* 3 No. 1.

Strenuous activities such as those engaged in sports, military or fire fighting actions can quickly elevate a person's body core temperature. Unless the body is suitably cooled off, excessive high body core temperature build up has contributed to heat stroke related fatalities. Traditionally, people who engage in such strenuous activities may wear active cooling garments such as liquid, ice, gas or air-cooled vest in order to relieve heat strain. The drawbacks of these garments are many—they are cumbersome and expensive, and cooling garments also increase insulation and, therefore, reduce sweat evaporation. As a result of added weight, these garments may even increase metabolic heat production.

Besides garments, other devices for cooling off body core temperature are not new. Hitherto, there were sun tanning tubs or pools which allow a user to partially immerse in water while sun bathing (see e.g., U.S. Pat. Nos. 5,101,823 and D447,807). Likewise, there are floating pool chairs which permit a user to sit on them while floating in water (see e.g., U.S. Pat. No. 6,045,423). Clearly, it is neither realistic nor appropriate for persons who suffer from high heat strain while engaging in vigorous sports, military actions or fire fighting activities to use the sun tanning tubs or pool chairs to cool themselves off.

According to recent studies (House et al. 1997; House 1998), heat strain prevention can be effectively achieved by immersing a person's extremities in water. For instance, House et al. examined the effectiveness of hand immersion in water at different temperatures as a technique for reducing heat strain in test subjects. Four subjects exercised at a moderate work rate whilst wearing fire-fighting clothing in an environmental chamber at 40° C. The subjects reached heat strain safety limits within 45 minutes of commencing work at which point they rested in the heat for 30 minutes while they underwent one of four experimental conditions: without intervention (control); or with their hands immersed in water at 10° C., 20° C. or 30° C., respectively. During the control condition without hand immersion the subjects were unable to cool. Immersion of the hands in water lowered body core temperature within ten minutes. These results indicate that hand immersion in water at a temperature of between 10° C. and 30° is an efficient means of cooling heat stressed personnel who have been exercising.

In view of the foregoing, it is advantageous to have a chair equipped with one or more water basins for heat strain reduction whereby the user can simply immerse his forearms and hands and, optionally, his feet into the basins filled with cold tap water. Such an inexpensive and convenient chair enables people who engage in strenuous activities to sit down and to submerge their extremities in water for a short period of time to allow their body core temperature to come down.

While there have been invented chairs with cooler or refrigerating functions (see e.g., U.S. Pat. Nos. 4,719,764, 5,628,544 and 6,106,058), a chair equipped with water basins for heat strain reduction was simply not thought of before. The closest art are U.S. Pat. No. 5,722,596, which teaches a mist-emitting lounge chair and U.S. Pat. No. 5,387,181, which discloses a lounge chair with a trough underneath for water circulation in order to emanate sounds simulating those of a running brook and, at the same time, to emit mist and negative ions into the air to concoct a "stress-relieving environment". However, sitting on one of these mist-discharging chairs does not help a user to lower his body core temperature to any significant degree. In addition, the need to wear proper clothing also renders these chairs impractical for users engaging in military or fire fighting activities.

SUMMARY OF THE INVENTION

It is an object of the present invention to solve the aforementioned problems by providing a chair equipped with built-in or attachable water basins for a user to reduce his body core temperature by simply immersing his forearms and hands into the water-filled basins.

According to one aspect of the invention, it provides a heat strain reduction chair with one or two water basins attached at the armrest level of the chair.

It is another object of the present invention to provide a water basin positioned in front or near the legs of a chair to enable a user to immerse his feet in the water-filled basin to decrease his body core temperature. According to another aspect of the invention, it provides a heat strain reduction chair with a water basin for a user's feet to be immersed therein.

It is yet another object of the present invention to provide a stand-up feet and/or arm heat strain reduction water pools for individual or multiple users to immerse their feet and/or arms in the pools to decrease their body core temperature. According to still another aspect of the invention, it provides a stand-up heat strain reduction pool system comprising a hand immersion pool and a foot immersion pool wherein the dimension of the foot pool is substantively larger than the hand immersion pool.

BRIEF DESCRIPTION OF THE DRAWINGS

FIG. 4b is a top partial-sectional view of the chair and foot basin shown in FIG. 4a.

DETAILED DESCRIPTION OF THE PREFERRED EMBODIMENTS

The present invention incorporates the concept of a water basin or basins built into or attached onto a portable folding lounge chair in order to allow a user to cool off his body core temperature by immersing his extremities in the water basins while the user sits down. The basins can be long and shallow, thus enabling a user to rest and immerse his forearms and hands substantially horizontally inside the basins. Alternatively, the basins can be short and deep to allow a user to simply drop and immerse his hands and forearms vertically inside the basins. The present invention also discloses a stand-up heat strain reduction water pool system for single or multiple users to immerse their arms and hands and, optionally, their feet in the pool filled with water.

Figure 1A:
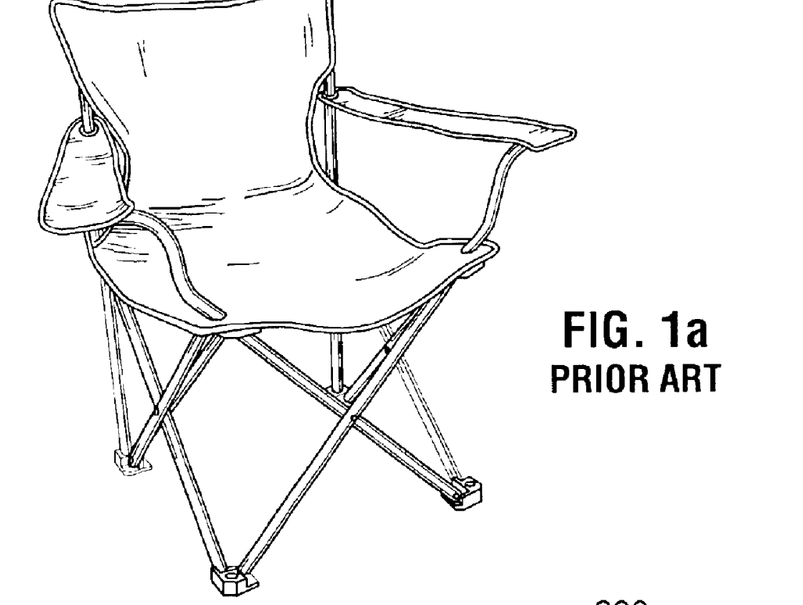
FIG. 1a is a perspective view of a conventional prior art folding lounge chair.

FIG. 1a shows a conventional prior art folding lounge chair.

Figure 1B:
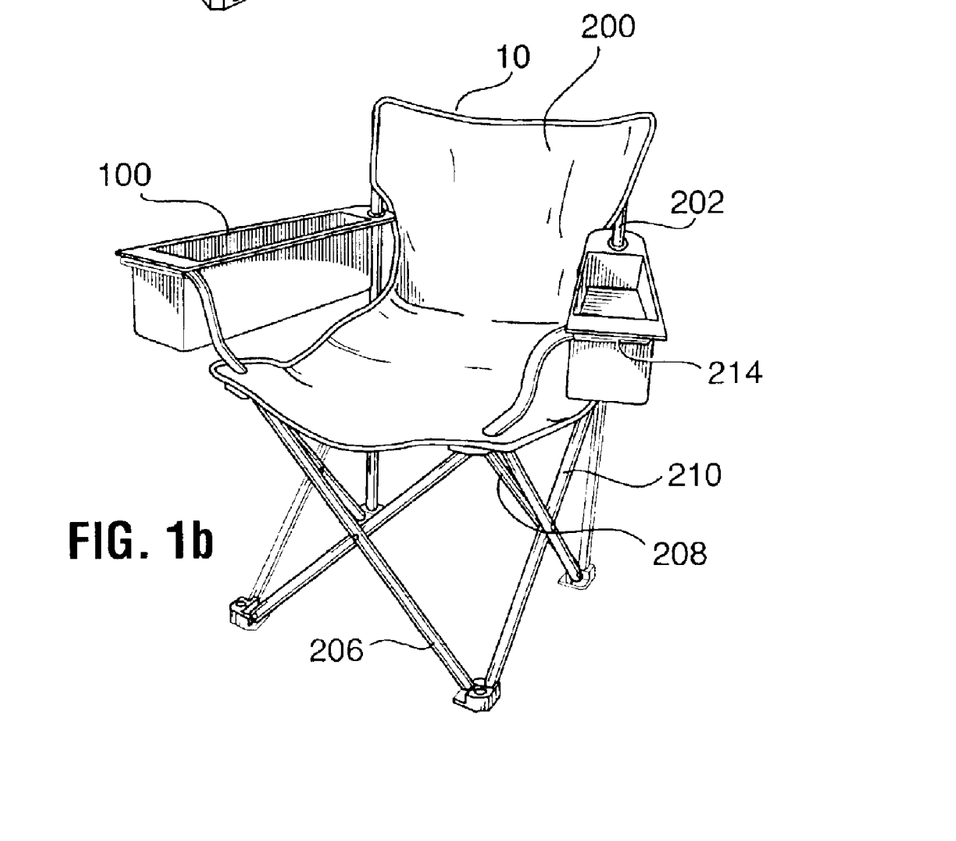
FIG. 1b shows a perspective view of a preferred embodiment of the instant invention.

A heat strain reduction chair 10 with two forearm and hand water basins according to the present invention is shown in FIG. 1b. The chair 200 is a typical folding lounge chair as shown in FIG. 1a with front crossed legs 206, rear crossed legs 208, side crossed legs 210 and rear leg side support poles 202. In addition, there is a water basin support pole 214 extending from the front crossed legs 206 through an opening in the chair seat upwardly and then horizontally parallel to the front plane of the chair.

Figure 2A:
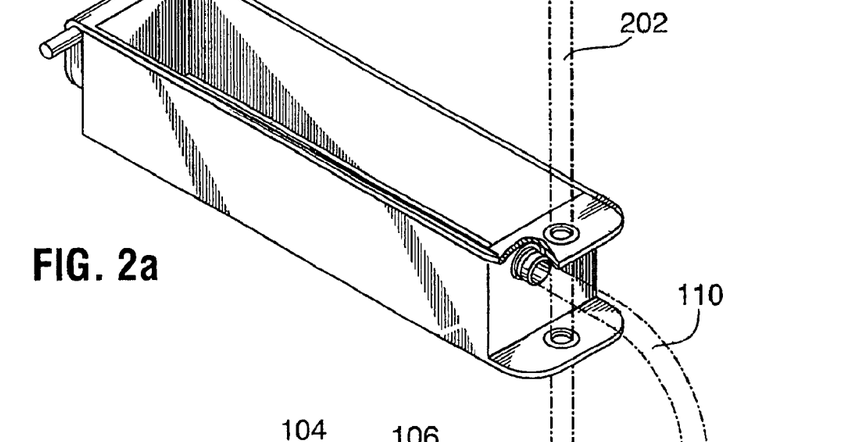
FIG. 2a is a perspective rear-side view of a preferred embodiment of a water basin for horizontal immersion.
Figures 2B, 2C:
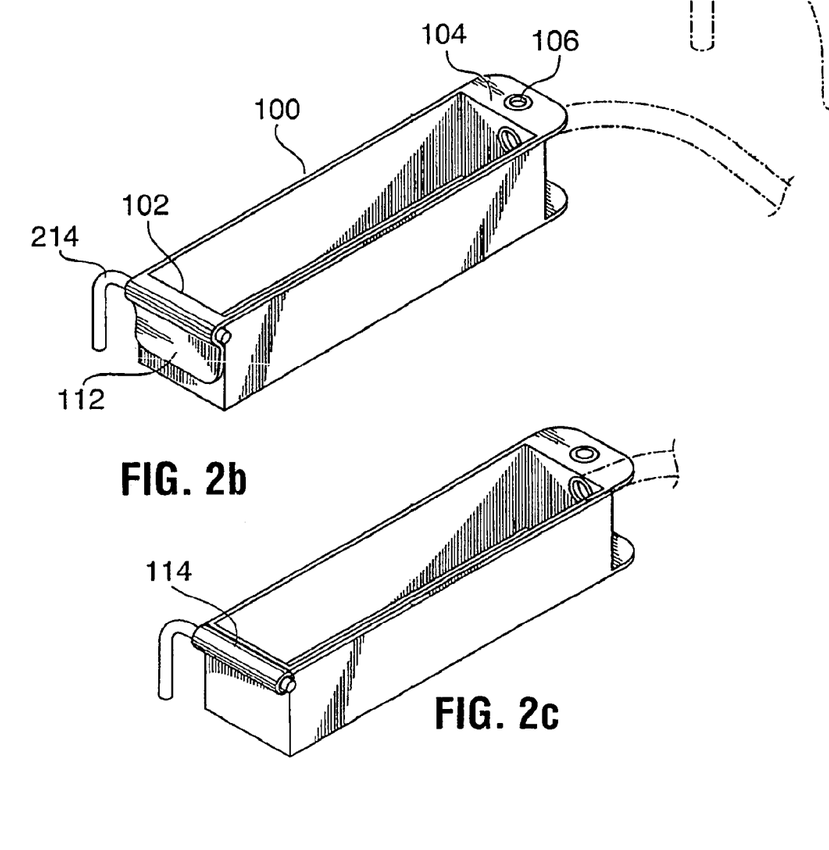
FIG. 2b is a perspective front-side view of a preferred embodiment of a water basin for horizontal immersion.
FIG. 2c shows a perspective front-side view of another embodiment of a water basin for horizontal immersion.

The horizontal portion of the water basin support pole 214 and the rear leg side support pole 202 cooperate together to allow the water basin 100 to be mounted on chair 200 as shown in FIG. 1b. FIGS. 2a and 2b illustrate this mounting set up. The horizontal water basin 100 has two ends, namely the distal end 102 for detachably mounted on the horizontal portion of support pole 214, and the proximate end 104 for slidably engaging onto the rear leg side support pole 202 through passage holes 106 provided at the proximate end. Distal end 102 can be mounted to support pole 214 by conventional means, such as by using Velcro™ flap 112 as shown in FIG. 2b, or by sliding sleeve 114 onto support pole 214 as shown in FIG. 2c.

A water fill up faucet 108 is optionally provided to water basin 100 with a flexible water hose 110 connected thereto. Preferably, faucet 108 and water hose 110 are at the proximate end 104. If desired, the user can connect water hose 110 to the water supply main and fill up the basin with household tap water. As discussed above, researches have shown that immersing a user's extremities in room temperature water can advantageously lower the body core temperature.

Figure 2D:
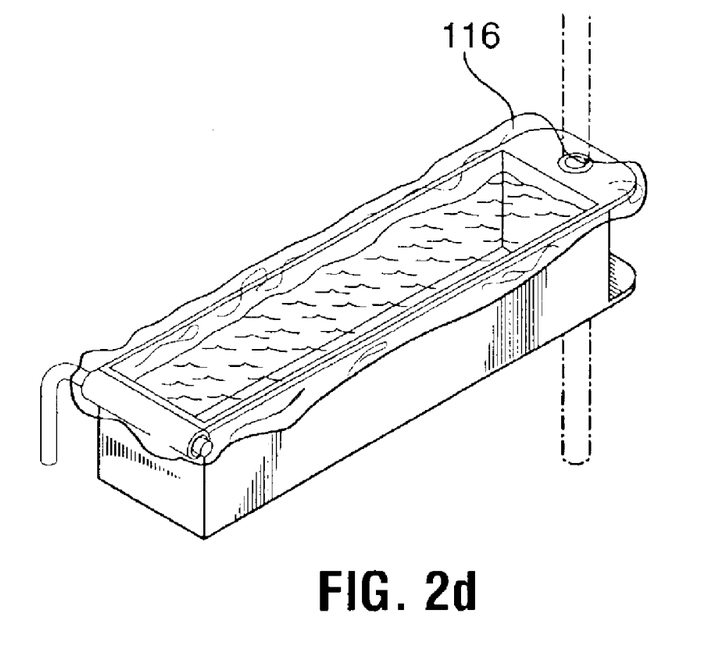
FIG. 2d shows a horizontal water basin with a disposable plastic lining.

For hygienic reason, FIG. 2d shows a disposable plastic liner 116 being inserted into water basin 100 for holding water. After use, the basin can be emptied and a new liner inserted therein for the next user.

Figure 2E:
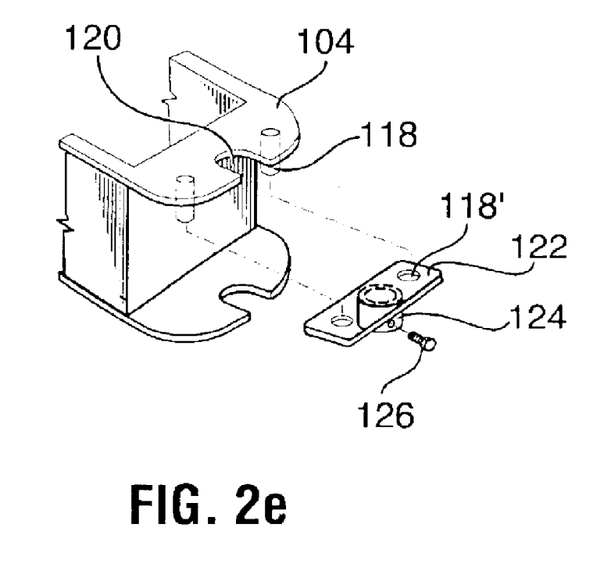
FIG. 2e shows a "pin-and-plate" securing means for a detachable horizontal water basin.

The present invention also provides a detachable water basin for heat strain reduction. FIG. 2e illustrates the detachable mounting mechanism by a "pin-and-plate" locking means provided at the proximate end 104 of the basin 100. The securing means is comprised of a pair of downward pin 118 positioned on both sides of a U-shaped notch 120. Plate 122 is slidably inserted into the rear leg side support pole 202 through pole mounting ring 124 and locked in position by tightening screw 126. Once securely fastened, the U-shaped notch 120 of the basin is placed against pole 202 while holes 118' on plate 122 couple with pins 118 on the underside of the water basin 100. To detach the water basin, the user simply lifts pins 118 from plate 122 and releases the Velcro™ flap at the distal end from horizontal support pole 214.

Figure 3:
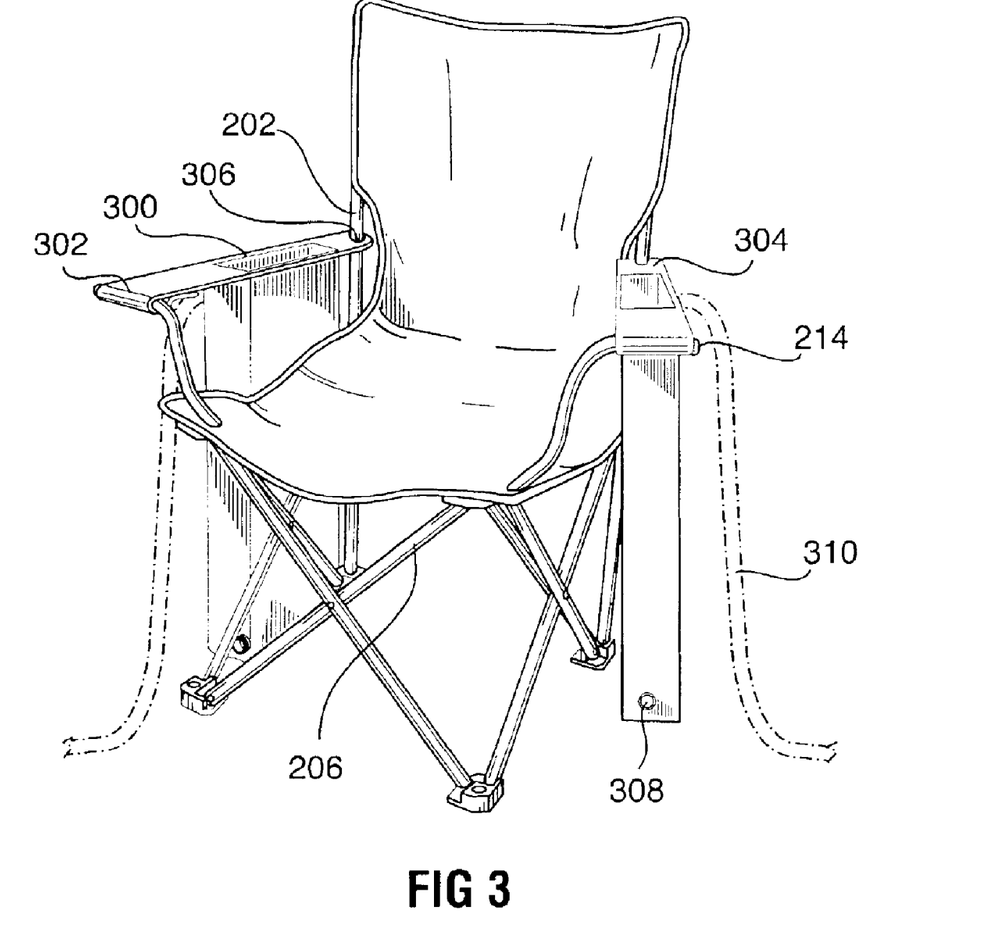
FIG. 3 is a perspective side view showing a chair with water basins for vertical immersion.

FIG. 3 illustrates another embodiment of the water basins being mounted to a folding lounge chair. Instead of a long and shallow basin discussed earlier, this embodiment provides for a short and deep basin for vertical immersion of a user's forearm and hand. The structural set up of this vertical basin 300 resembles the horizontal basin. As is in the case of the horizontal basin, there is provided a side water basin support pole 214 extending from the front crossed legs 206 through an opening in the chair seat upwardly and then horizontally along the front plane of the chair. Distal end 302 of the vertical basin 300 is detachably mounted to support pole 214 by a sliding sleeve (as shown) or a Velcro™ flap (not shown). Since the proximate-distal distance of the opening of vertical basin 300 is much shorter, a substantially flat portion of basin material is provided to connect the basin opening to the mounting flap at the distal end 302 which mounts to the horizontal portion of the support pole 214. At the proximate end 304, the slidably coupling arrangement is the same as those with the horizontal basin. The depth of the vertical basin may vary, as long as it can accommodate the length of a user's arm and hand. Optionally, the vertical basin may extend the depth all the way to ground level (as shown). In a preferred embodiment, vertical basin 300 is provided with water fill-up faucet (not shown) and host 310, and water release faucet 308.

Another embodiment of the chair of the present invention provides for a rigid frame substantially defining the dimension of the opening of the horizontal or vertical water basin (not shown). The frame is demountably attached to the support pole 214 at the distal end and rear leg side pole 202 at the proximate end. The rigid frame suitably receives a disposable plastic pouch which becomes a temporary water basin for users to immerse their hands and forearms.

Figure 4A:
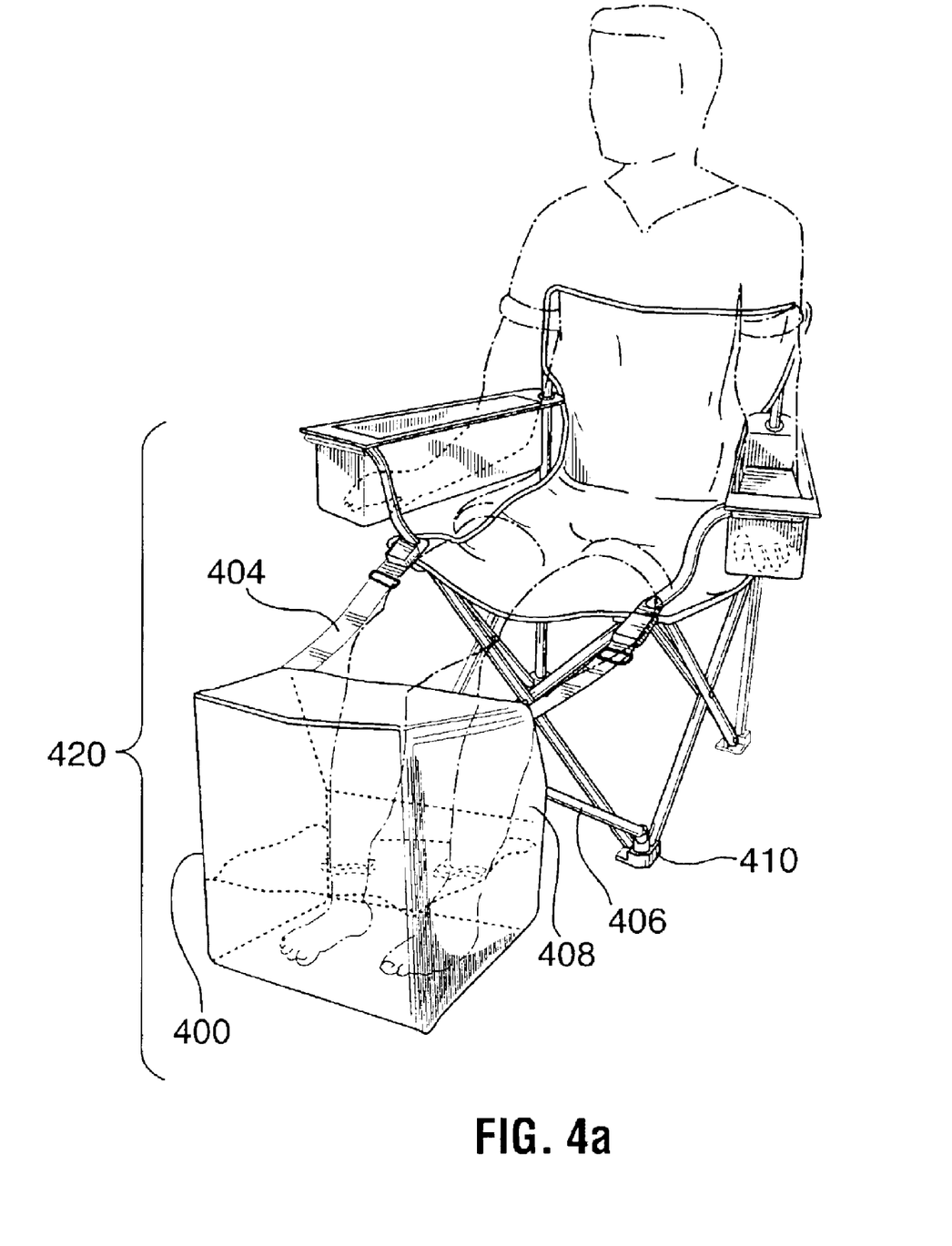
FIG. 4a shows a perspective view of another embodiment of the instant invention incorporating a heat strain reduction water basin for a user's feet with a user sitting thereon and the user's feet immersed in the water basins.
Figure 4B:
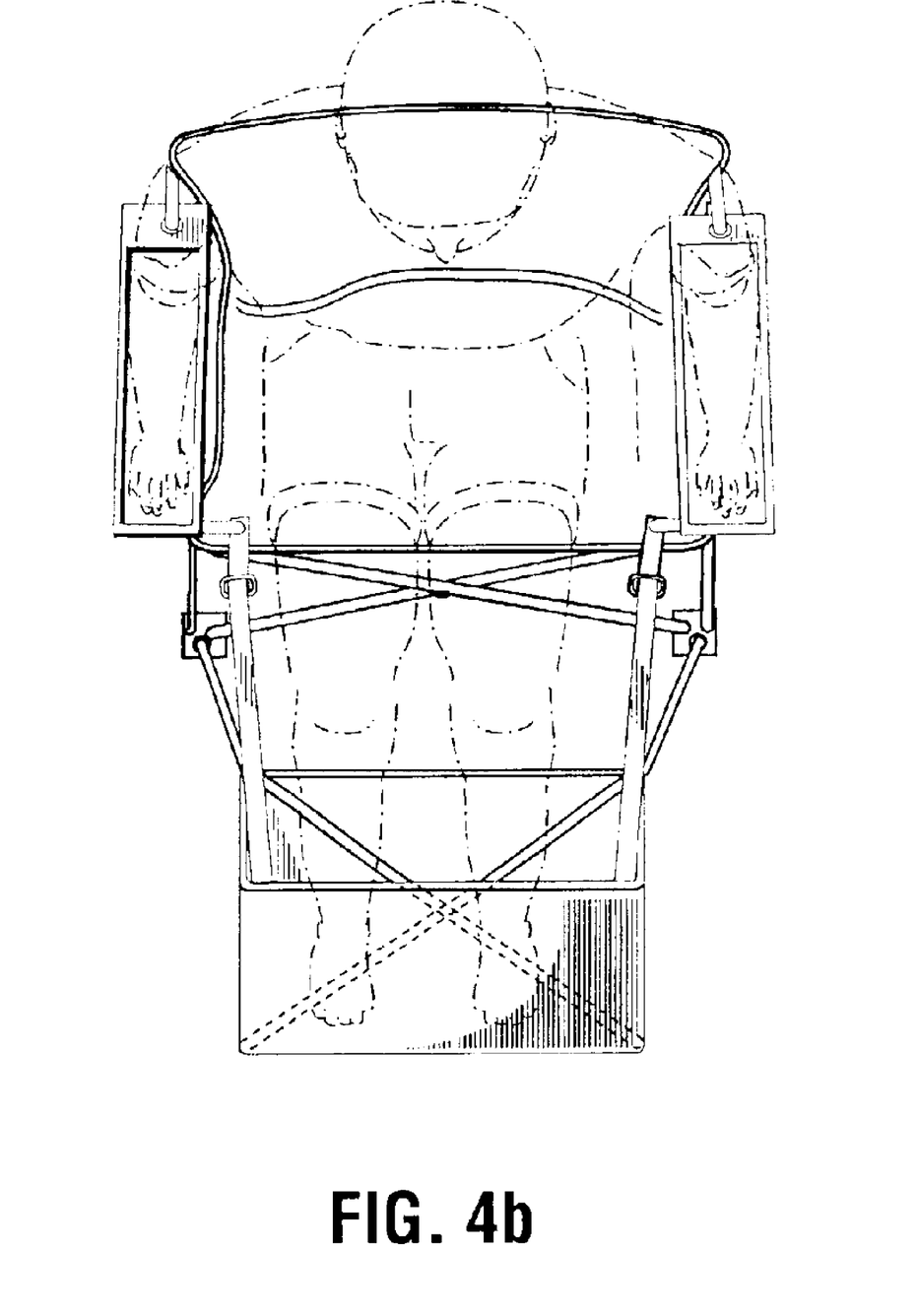

Researches have shown that a person's body core temperature decreases more rapidly if both extremities were immersed in water as opposed to only immersing a person's hands or feet. Accordingly, another embodiment of the present invention provides a heat strain reduction chair equipped with water basins for both hands and feet. FIG. 4a illustrates a perspective view of such a chair and FIG. 4b shows a top partial-sectional view with a user immersing his feet in the foot basin of the present invention. As can be seen from FIG. 4a, the "arm & foot" chair combines the inventive feature of the arm and hand basin chair discussed earlier with a foot basin attachment module 420 engaged thereto.

Referring to FIGS. 4a and 4b, foot basin attachment module 420 is comprised of a pair of chair foot basin crossed extension poles 406, extending from each corner of the front pole connector 410. The outward apex of the crossed extension pole 406 is extended to the opposite top distal end of the foot basin 400 (not shown). The general structure of foot basin 400 is defined by a rectangular pouch with an opening 408 on the proximate side facing the user's feet. The bottom side of foot basin 400 rests on the ground. A pair of fastening straps 404 secures the top proximate end of basin 400 to the top of the front crossed legs. When in use, a user sits on the chair and extends his feet forward into the water-filled foot basin 400 through opening 408. In so doing, the user rests his immersed feet on the ground.

Optionally, water release/fill up faucet and flexible hose can be provided (not shown) to the foot basin to ease use and operation.

Foot basin attachment module 420 can be detached from the hand basin chair by releasing fastening straps 404, which are furnished with a lockable means, such as a lug or hook, and by dislodging the foot basin crossed extension poles 406 from the front pole connector 410.

The support poles and legs of the heat strain reduction chair of the present invention are tubular and can be made of conventional materials such as aluminium, steel, fibre reinforced plastic or other such suitable materials. The water basin can be made of waterproof fabric, nylon, plastic, fibre reinforced plastic or any suitable flexible and collapsible materials. When not in use, the chair, together with the basins, can be folded up for easy storage.

For greater stability and to avoid toppling, anchoring means can optionally be used to secure the chair of the present invention to the ground. Suitable anchoring means include fastening pegs, water-filled mooring devices and the like.

Figure 5A:
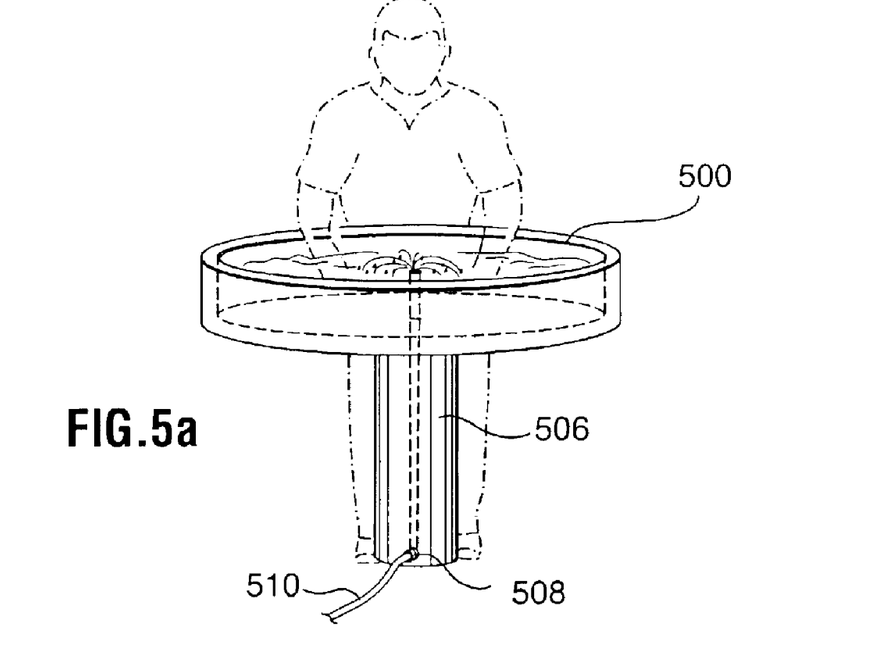
FIG. 5a shows a stand-up heat strain reduction water pool for hand immersion by users standing up.

There may be occasions in which a group of users may wish to benefit from heat strain reduction, e.g., after a game of sport or team activity. Accordingly, the present invention also provides for a stand-up heat strain reduction pool system. FIG. 5*a* illustrates a stand-up hand pool for immersing the users' hands whereas FIG. 5*b* illustrates a stand-up hand and foot pool.

Referring to FIG. 5*a,* hand pool 500 is supported by base 506. The base is, in turn, supported by conventional anchoring means. Suitable anchoring means (not shown) are cement blocks, water-filled mooring containers or embedment in the ground.

Figure 5B:
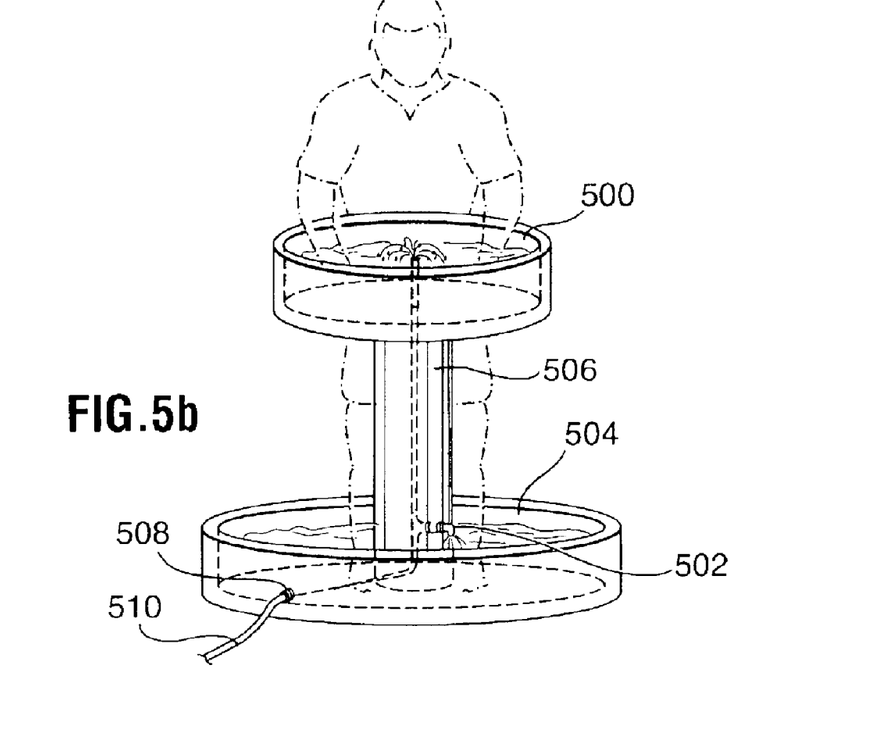
FIG. 5b shows stand-up heat strain reduction water pools for both hand and feet immersion by users standing up.

In the case of hand and foot pools shown in FIG. 5*b,* there is provided a hand pool 500 supported by base 506. The base of 506 abuts and is contiguous with foot pool 504 which sits on the ground. In order that the users can stand in the foot pool 504 and immerse their hands around the hand pool 500, the dimension of the foot pool 504 is measurably larger than the dimension of the hand pool 500. Once again, water-fill up faucet 502 and 508 and flexible water hose 510 are optionally provided to the pools. Clearly, the heat strain reduction pool of the present invention is not confined to circular shape. In fact, such a pool can take any shape as long as it enables the users to immerse their hands and/or feet therein.

As in the case of the horizontal basin, disposable plastic liner may be inserted into the vertical water basin or the foot basin for holding water in order to maintain hygienic use of the basin. After use, the basin can be emptied and replaced with a new liner. Disposal liner can be used for the hand and foot pools as well.

Since it is beneficial to enjoy the heat strain reduction chair in the shade, the present invention also provides a chair equipped with a collapsible umbrella similar to those used with beach chairs attached thereon (not shown).

It is clear that the inventive concept of this heat strain reduction chair is not limited to folding lounge chairs. Any conventional lounge chairs, whether foldable or not, and other chairs, such as director's chair and wheel chair (not shown), can incorporate the present inventive concept and provide for suitable water basins for either arm and hand only and/or arm and hand and foot immersion. Thus, the embodiments depicted herein are intended to be merely illustrative and not restrictive in any sense.

It is further understood that the present invention may be carried out in other specific way than those herein set forth without departing from the spirit and essential characteristics of such invention. The present embodiments are, therefore, to be considered in all respects as illustrative and not restrictive, and all changes coming within the meaning and equivalency range of the appended claims are intended to be embraced therein.

What is claimed is:

1. A heat strain reduction chair with one or two water basins attached at the armrest level of said chair, wherein said water basin is substantially long and shallow with a distal end for mounting onto a horizontal support means and a proximate end with means for slidably engaging a rear leg side support pole of said chair, said slidably engaging means comprised of one or more pins projecting in a direction substantially parallel to said rear leg and plate locking arrangement movably affixed to said rear leg side support pole, said plate locking arrangement have one or more orifices for receiving said pins.

2. The heat strain reduction chair of claim 1, wherein said horizontal support means is a pole extending from a front crossed leg of the chair.

\* \* \* \* \*